US009259256B2

(12) United States Patent
Gleason, Jr. et al.

(10) Patent No.: US 9,259,256 B2
(45) Date of Patent: Feb. 16, 2016

(54) METHOD AND APPARATUS FOR DELIVERY OF BONE CEMENT

(75) Inventors: Thomas James Gleason, Jr., Malmo (SE); Lars Ek, Trelleborg (SE); Steen Stavnshoj, Simrishamn (SE); Mats Rosengren, Sjobo (SE)

(73) Assignee: Biomet SAS (FR)

( * ) Notice: Subject to any disclaimer, the term of this patent is extended or adjusted under 35 U.S.C. 154(b) by 984 days.

(21) Appl. No.: 13/417,599

(22) Filed: Mar. 12, 2012
(Under 37 CFR 1.47)

(65) Prior Publication Data
US 2013/0158560 A1 Jun. 20, 2013

(51) Int. Cl.
A61B 17/88 (2006.01)
A61B 19/00 (2006.01)

(52) U.S. Cl.
CPC .......... *A61B 17/8811* (2013.01); *A61B 17/8816* (2013.01); *A61B 17/8822* (2013.01); *A61B 2019/307* (2013.01)

(58) Field of Classification Search
CPC ........... A61B 17/8802; A61B 17/8805; A61B 17/8811; A61B 17/8825; A61B 1717/8822; A61B 17/8827; A61B 17/8841; A61B 17/00491
See application file for complete search history.

(56) References Cited

U.S. PATENT DOCUMENTS

| | | | | |
|---|---|---|---|---|
| 4,466,435 A * | 8/1984 | Murray | ............................ | 606/94 |
| 4,815,454 A * | 3/1989 | Dozier, Jr. | ........................ | 606/94 |
| 5,370,221 A | 12/1994 | Magnusson et al. | | |
| 5,741,265 A * | 4/1998 | Chan | ................................ | 606/94 |
| 6,190,392 B1 | 2/2001 | Vandewalle et al. | | |
| 2007/0016216 A1 | 1/2007 | Tague et al. | | |

FOREIGN PATENT DOCUMENTS

| | | |
|---|---|---|
| DE | 9319325 U1 | 2/1994 |
| DE | 10005105 A1 | 8/2001 |
| DE | 20120080 U1 | 4/2003 |
| EP | 1749586 A1 | 2/2007 |
| WO | WO-0126824 A1 | 4/2001 |

OTHER PUBLICATIONS

Biomet "Different Solutions—Great Results" brochure, 8 pages, 2010.
Biomet Optivac Vacuum Mixing System Brochure, 2 pages, Jan. 1, 1996.
Biomet Optivac® Kits for the US Market, 4 pages.
Biomet Optivac® Vacuum Mixing System retrieved from URL www.biomet.com/orthopedics/productDetail.cfm?category=7&product=224 on Jan. 30, 2012, 1 page.
German Search Report mailed Oct. 5, 2012 for German patent Application No. 202012002829.4 filed Mar. 21, 2012 claiming benefit of U.S. Appl. No. 13/417,599, filed Mar. 12, 2012.
Great Results Optipac, Optivac and Biomet Bone Cements retrieved from URL www.bonecement.com/home on Jan. 30, 2012, 1 page.
Hip Acetabular Pressurization Biomet Cement and Cementing Systems retrieved from URL www.bonecement.com/products/pressurization/hip-acetabular on Jan. 30, 2012, 1 page.
Hip Femoral Pressurization Biomet Cement and Cementing Systems retrieved from URL www.bonecement.com/products/pressurization/hip-femoral on Jan. 30, 2012, 2 pages.
Knee Pressurization Biomet Cement and Cementing Systems retrieved from URL www.bonecement.com/products/pressurization/knee/ on Jan. 30, 2012, 1 page.
Optipac® Biomet product listing, 2 pages, 2005.
Optivac® Kits for the US Market, Biomet, 4 pages, 2005.

\* cited by examiner

*Primary Examiner* — Anu Ramana
(74) *Attorney, Agent, or Firm* — Schwegman Lundberg & Woessner, P.A.

(57) ABSTRACT

A method of applying bone cement for an orthopedic procedure of a patient includes coupling a proximal end of a nozzle component to a bone cement applicator and applying bone cement on a surface of an implant or on a bone surface through an elongated distal opening of a distal portion of the nozzle component. The method includes separating the distal portion from an intermediate portion of the nozzle component at a frangible connecting portion and exposing a circular distal end of the intermediate portion.

18 Claims, 7 Drawing Sheets

METHOD AND APPARATUS FOR DELIVERY OF BONE CEMENT

CROSS-REFERENCE TO RELATED APPLICATIONS

This application claims the benefit and priority of European Community Design Registration No. 001307532-0001 filed Dec. 20, 2011. The entire disclosure of the above application is incorporated herein by reference.

FIELD

The present disclosure relates to a bone cement apparatus and associated method for applying and delivering bone cement.

INTRODUCTION

This section provides background information related to the present disclosure which is not necessarily prior art.

In various orthopedic applications, including knee, hip, shoulder, or other arthroplasty, bone cement can be used to anchor and stabilize an implant relative to a corresponding bone. Bone cement can be prepared in a mixer or in a mixer integrated with a bone cement cartridge. The cartridge can be attached to a bone cement nozzle and delivered using a bone cement gun or other bone cement applicator.

SUMMARY

This section provides a general summary of the disclosure, and is not a comprehensive disclosure of its full scope or all of its features.

The present teachings provide a method of applying bone cement for an orthopedic procedure of a patient. The method includes coupling a proximal end of a nozzle component to a bone cement applicator and applying bone cement on a surface of an implant or on a bone surface through an elongated distal opening of a distal portion of the nozzle component. The method includes separating the distal portion from an intermediate portion of the nozzle component at a frangible connecting portion and exposing a circular distal end of the intermediate portion.

In another embodiment, the method includes coupling a proximal end of a nozzle component to a bone cement applicator. The nozzle component includes an elongated intermediate portion having a linearly variable circular cross-section, a connecting portion extending from the intermediate portion at a frangible location and a distal portion having an elongated cross-section. Flat strips of bone cement are applied on a surface of a first bone or a first implant through an elongated distal opening of the distal portion of the nozzle component. Each flat strip can have a predetermined width and thickness. The method includes breaking the distal portion off the intermediate portion of the nozzle component at the frangible location to form a distal end with a circular cross-section, and filling a hole of a second bone with bone cement delivered from the circular cross-section. The first bone can be the same as the second bone.

The present teachings provide an apparatus for bone cement delivery that includes a nozzle component having a proximal end configured to be coupled to a bone cement applicator. The nozzle component includes an elongated intermediate portion having a linearly variable circular cross-section, a connecting portion extending from the intermediate portion at a frangible location defined by a circular groove and a distal portion having an elongated cross-section. The elongated cross-section is configured to deliver strips of bone cement having predetermined width and thickness. The circular groove is configured to define a circular distal end after the distal portion is broken off.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
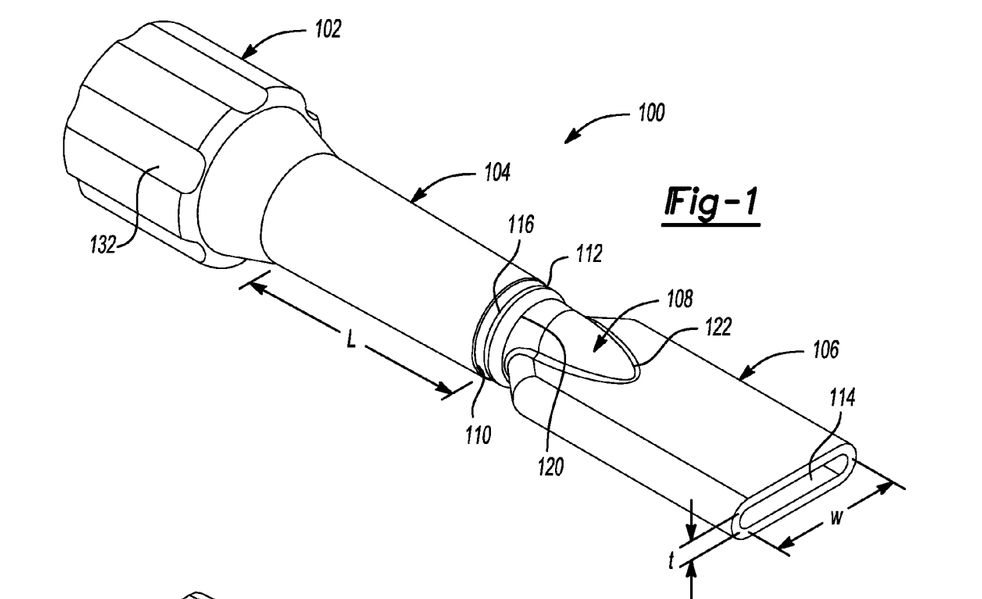
FIG. 1 is a perspective view of a bone cement nozzle according to the present teachings.
Figure 2:
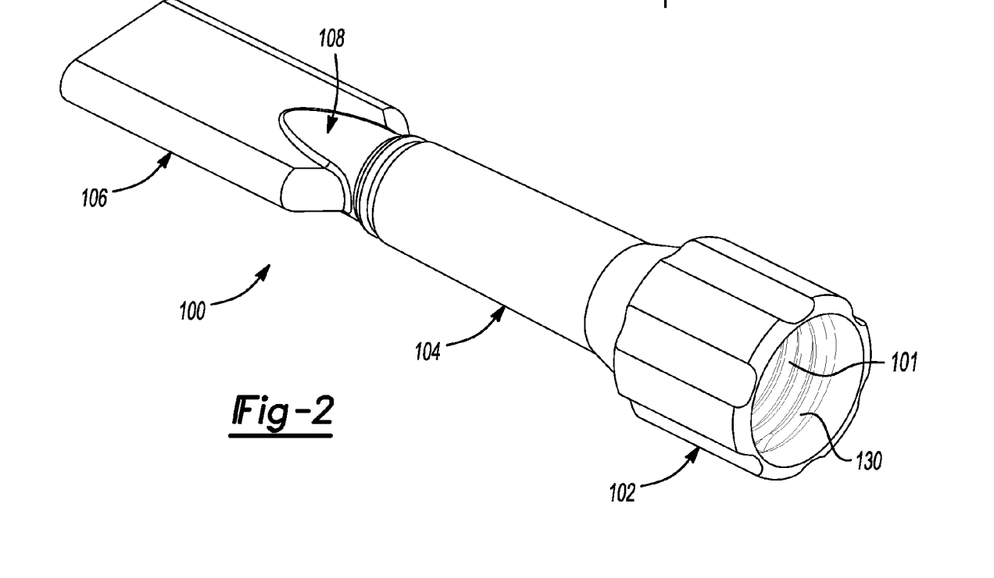
FIG. 2 is another perspective view of the bone cement nozzle of FIG. 1.
Figure 3A:
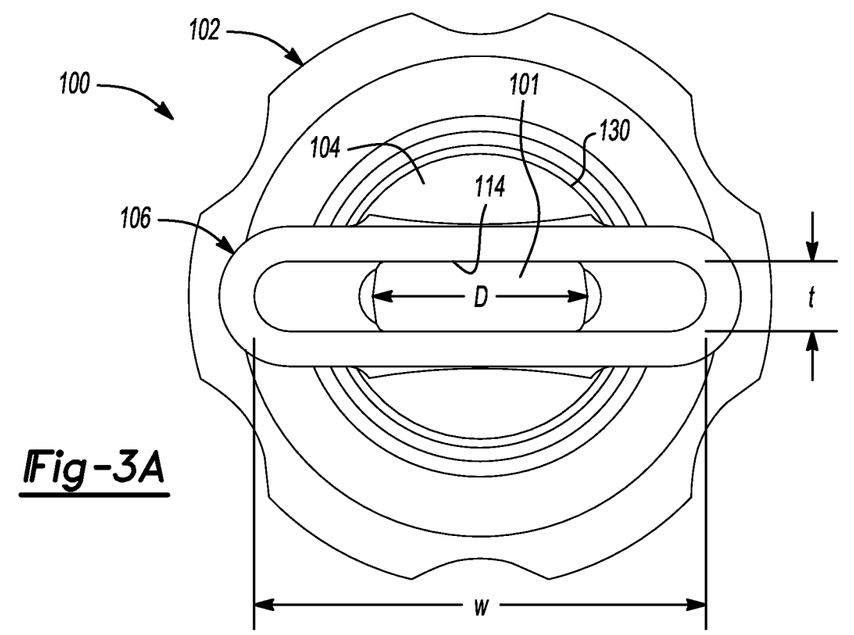
FIG. 3A is a front end view of the bone cement nozzle of FIG. 1.
Figure 3B:
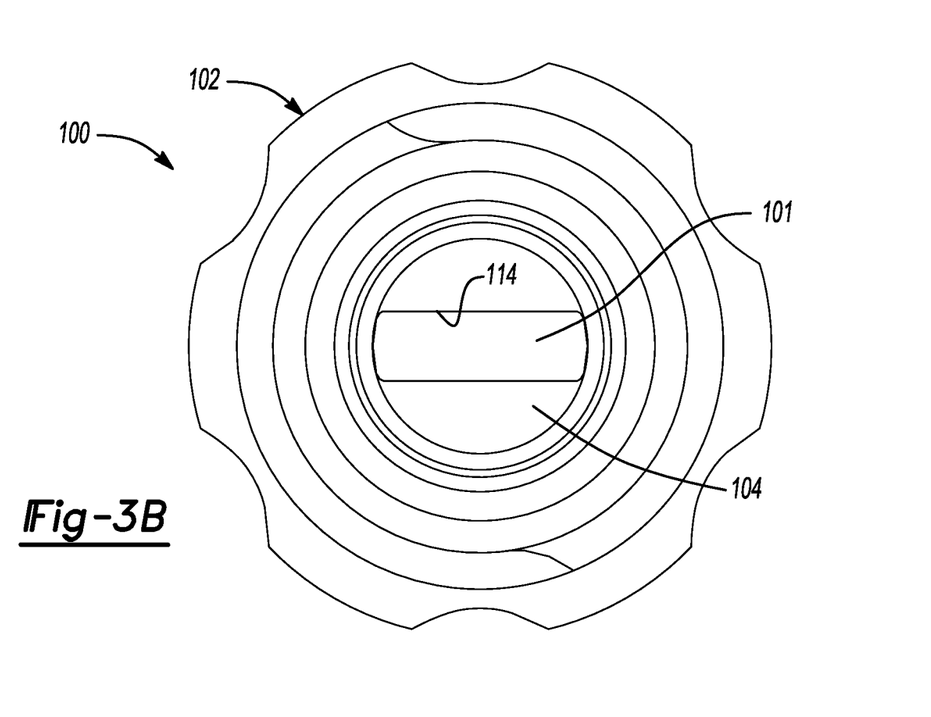
FIG. 3B is a rear end view of the bone cement nozzle of FIG. 1.
Figure 7:
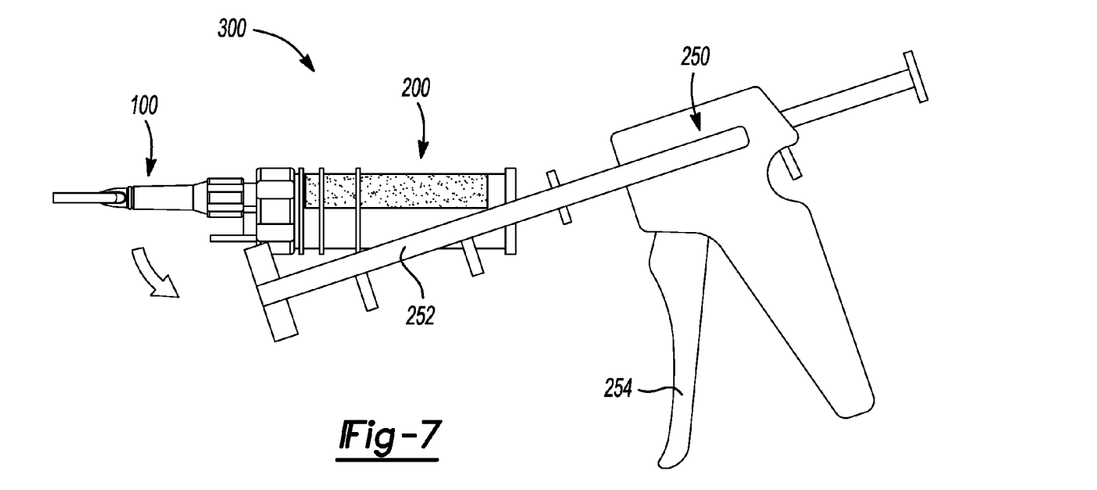
FIG. 7 is a perspective view of the bone cement nozzle and cartridge of FIG. 6 loaded to a bone cement gun.

The present teachings provide a bone cement nozzle 100 (see FIG. 1) that can be used with a bone cement applicator 300, such as a bone cement cartridge 200 that can be loaded on an arm 252 of a bone cement gun 250 or other bone cement delivery device, as shown in FIG. 7. The bone cement gun 250 shown in FIG. 7 is operated with a pump-type trigger action using a trigger 254.

The bone cement nozzle of the present teachings has a frangible distal portion 106 (FIG. 1) with a distal end configured to provide flat or substantially planar strips of bone cement on a bone surface or on an implant surface in preparation for arthroplasty, such as knee, hip, shoulder, or other joint of a patient. The bone cement nozzle 100 of the present teachings includes a breakaway location 110 (FIG. 1) that facilitates breaking off the distal portion 106 of the bone cement nozzle 100 to expose a new distal end (FIG. 12) suitable for filling holes and/or providing bone cement in smaller or deeper areas of a bone, such as, for example, an intramedullary canal. In this respect, the bone cement nozzle 100 can provide bone cement in a first shape that is substantially in the form of an elongated cylinder, and in a second shape that is in the form of a flat or substantially planar strip.

Referring to FIGS. 1-7, the bone cement nozzle 100 of the present teachings provides a channel 101 for delivering bone cement. The bone cement nozzle 100 can include a first or proximal portion 102, a second or intermediate portion 104, a third or distal portion 106 and a connecting or transitional portion 108 between the intermediate portion 104 and the distal portion 106. The channel 101 runs through each of the above portions, 102, 104, 108 and 106. The proximal portion 102 can be configured for coupling to a bone cement cartridge 200 and/or generally to a bone cement applicator 300 (FIG. 7). The intermediate portion 104 is an elongated tubular portion with a cross-section that can be either constant along its length or variable or tapered along its length. In some embodiments, the intermediate portion 104 can be a hollow cylinder with an inner wall 105 and with a circular, round or other closed curve cross-section that remains longitudinally constant. In other embodiments, the intermediate portion 104 can be in the form of a truncated cone with a longitudinally linearly variable or tapered circular cross-section.

Figure 8:
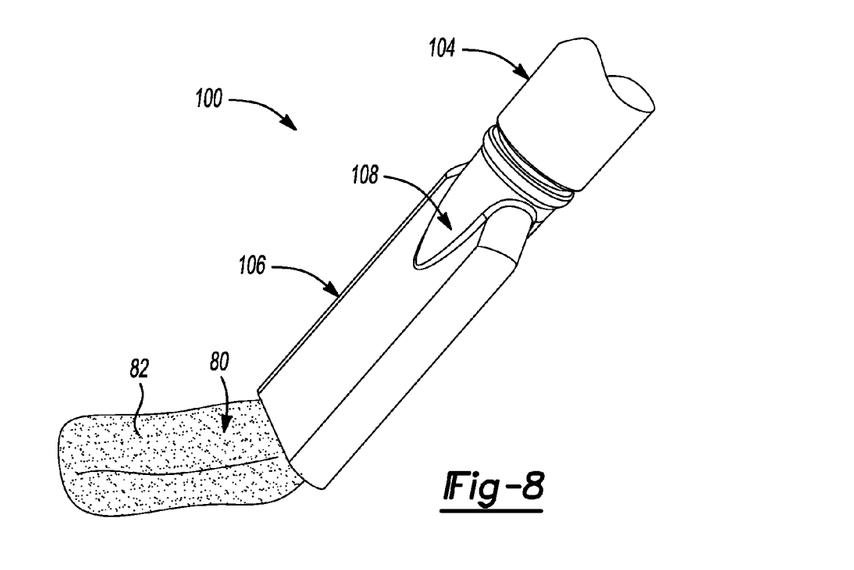
FIG. 8 is a perspective view of a bone cement nozzle according to the present teachings showing delivery of a flat strip of bone cement.
Figures 9, 10:
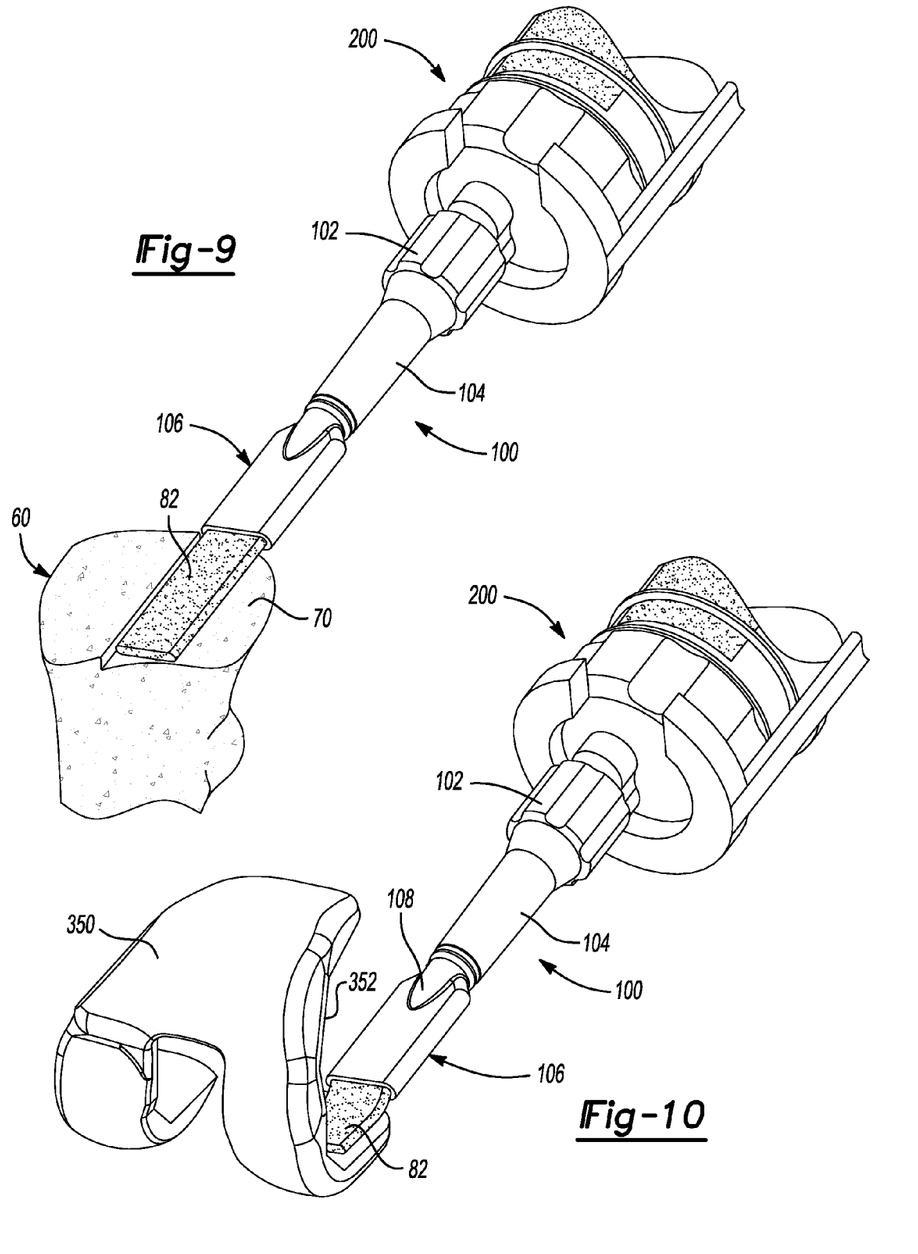
FIG. 9 is a perspective environmental view of a bone cement nozzle according to the present teachings showing an application of flat strips of bone cement to a tibial bone surface in preparation for a knee implant.
FIG. 10 is a perspective environmental view of a bone cement nozzle according to the present teachings showing an application of flat strips of bone cement to a femoral knee implant.

The distal portion 106 is plate-like and has an elongated cross-section with an elongated distal opening 114 having a width "W" and a thickness "t" for delivering flat strips of bone cement having corresponding predetermined width W and thickness t. The cross-section can be, for example, in the form of an elongate rectangle with or without rounded corners, or an elongated ellipse or other elongated shape that can deliver substantially flat and wide strips 82 of bone cement 80 for covering substantially uniformly and easily a bone surface and/or an implant surface, as shown in FIGS. 8, 9 and 10, and discussed below. In other words, the bone or implant surface can be covered with a flat layer of bone cement having a predefined thickness without having to manipulate the bone cement after it is delivered to the site from the bone cement nozzle 100.

Figure 4A:
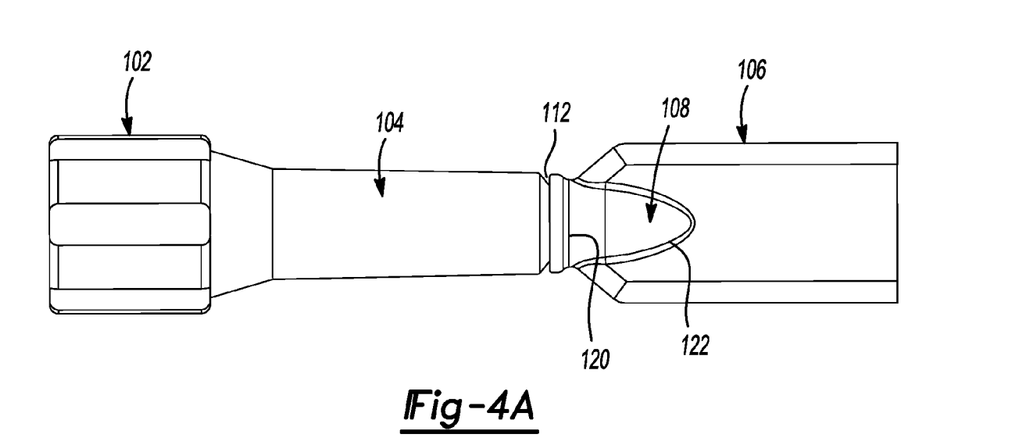
FIG. 4A is a plan view of another embodiment of bone cement nozzle according to the present teachings.
Figure 4B:
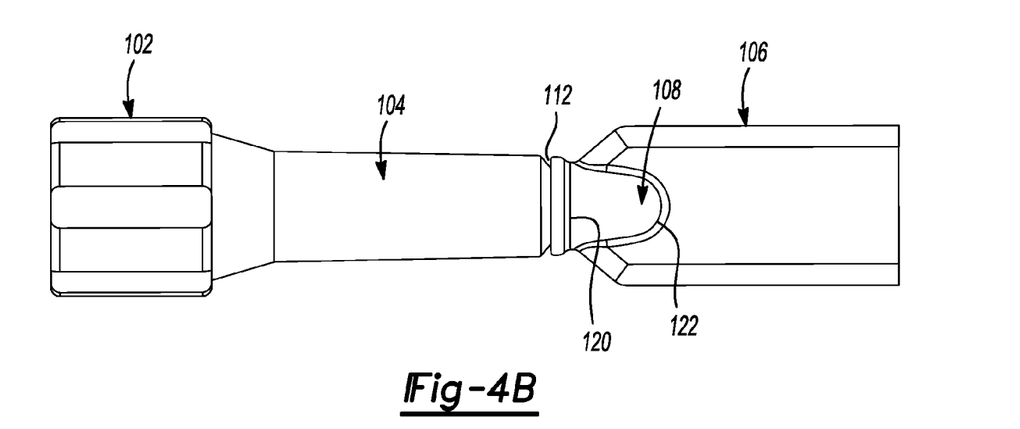
FIG. 4B is a plan view of another embodiment of bone cement nozzle according to the present teachings.
Figure 5:
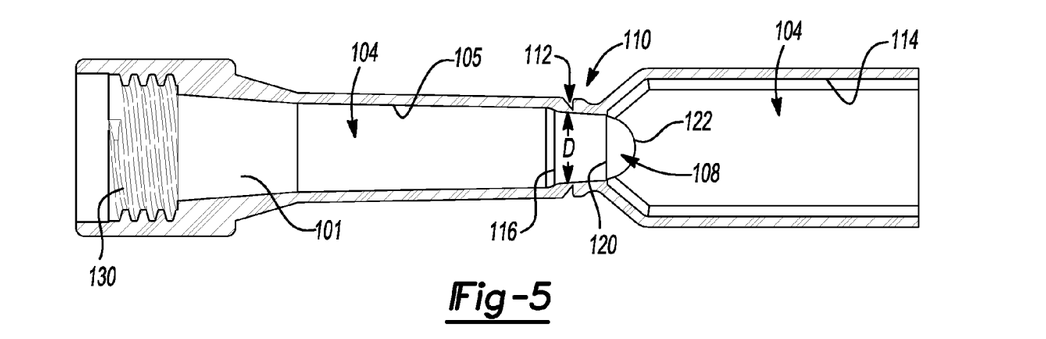
FIG. 5 is a sectional view of another embodiment of bone cement nozzle according to the present teachings.
Figure 6:
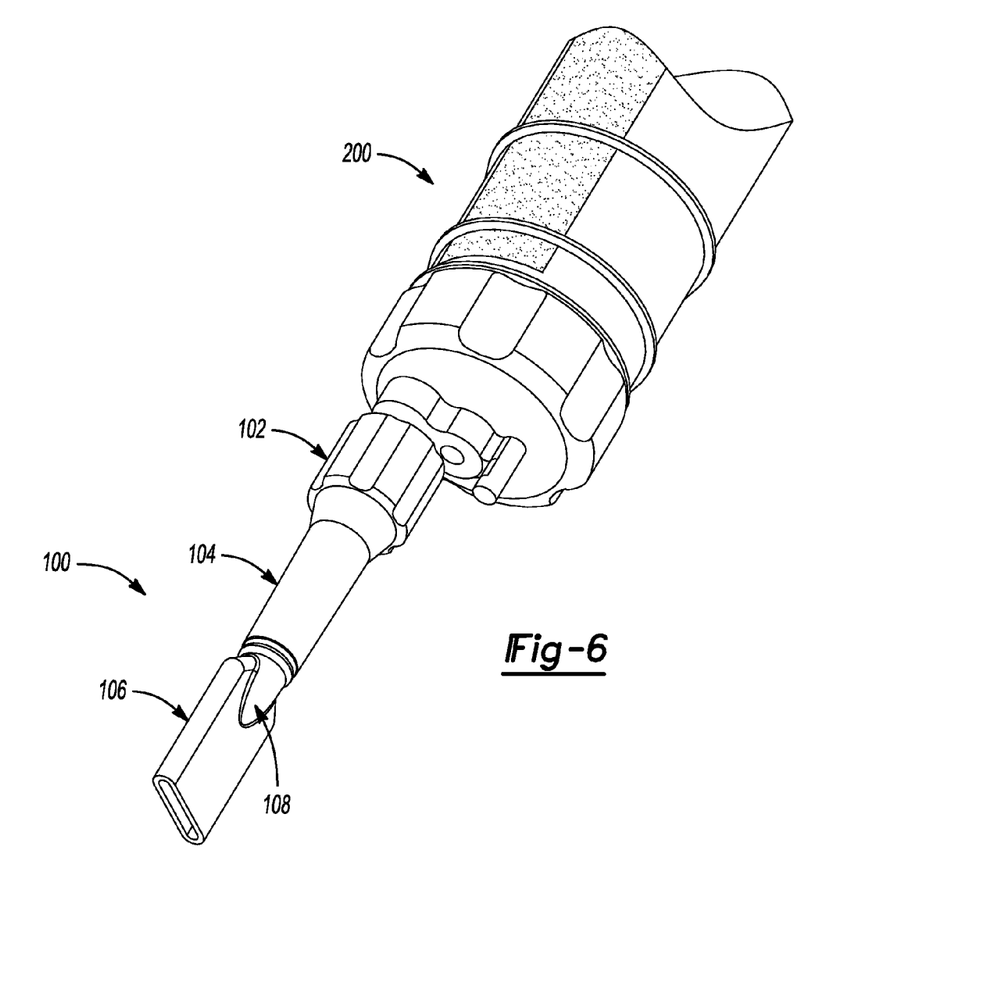
FIG. 6 is a perspective view of the bone cement nozzle of FIG. 1 shown attached to a bone cement cartridge.

Referring to FIGS. 1-8, the distal portion 106 can be broken off and separated from the intermediate portion 104 at a frangible location 110. The frangible location 110 can be a thinned area that can include a groove or other indentation 112 specifically configured to provide a clean break (FIG. 5). A clean break, as used herein, provides a substantially smooth edge, without jagged or hanging torn portions. Accordingly, the same bone cement nozzle 100 can be used to deliver and apply bone cement in either one of two shapes or configurations, i.e., from the elongated distal opening 114 of the distal end portion 106 and/or from a round or circular distal opening 116 of the intermediate portion 104 after the distal portion 106 is broken off and removed from the bone cement nozzle 100. The elongated distal opening 114 can be used to deliver flat strips 82 of bone cement 80 (FIG. 8) for covering bone or implant surfaces. The circular distal opening 116 has a diameter D that is smaller than the width W of the elongated distal opening 114 and can be used to deliver bone cement 80 into holes in bone, such as stem holes, peg holes, anchoring holes or other openings for implant fixation, as well into intramedullary bone canals or on to small, tight access areas of a bone or implant surface. In this respect, a single bone cement nozzle 100 can be used without the need to change nozzles depending on the application.

The bone cement nozzle 100 can be provided in different sizes and configurations for different arthroplasty applications. For example, for knee arthroplasty, the intermediate portion 104 can have a length L that is shorter than a similar length L for a bone cement nozzle 100 to be used in acetabular or hip arthroplasty procedures. Additionally, a plurality of frangible locations 110 (not shown) can be provided along the length L of the intermediate portion when the bone cement nozzle 100 is used for procedures requiring a deeper reach into the bone. In this respect, the appropriate length can be selected by breaking the intermediate portion 104 along a one of the frangible locations 110. The connecting portion 108 can also have a variety of shapes and sizes, as discussed below.

The connecting portion 108 can bulge or protrude outward from the distal end portion 106. The connecting portion 108 can be, for example, funnel-like with a wide end portion 120 directed toward the intermediate portion 104 and a narrow end portion 122 of the funnel embedded in distal portion 106. The funnel-like shape of the connecting portion 108 can be configured as a built-in pressurizer that can provide different degrees of pressurization to the bone cement 80, as illustrated in FIG. 4A, FIG. 4B and FIG. 5, in which exemplary connecting portions 108 with different shapes, curvatures and dimensions are shown.

Referring to FIGS. 1-5, the proximal portion 102 can be configured for coupling with a bone cement cartridge, such as the bone cement cartridge 200 and/or a bone cement applicator 300. For example, the proximal potion 102 can include internal threads or other internal formations 130 or other coupling mechanisms for coupling with a bone cement cartridge 200. Outer formations 132 of the proximal portion 102 can be configured for manual gripping and rotating the bone cement nozzle 100.

Referring to FIGS. 9-12, exemplary methods of using the bone cement nozzle 100 are illustrated. In FIG. 9, for example, the bone cement nozzle 100 is used to apply flat strips or ribbons 82 of bone cement on a resected surface 70 of a tibial bone 60 in preparation for receiving a knee tibial implant (not shown). Alternatively, the bone cement can be applied on a flat bone-engaging surface of a tibial tray. In FIG. 10, the bone cement nozzle 100 is used to apply flat strips 82 of bone cement on an inner, bone-engaging surface 352 of a knee femoral implant in preparation for knee arthroplasty. Similarly, bone cement can be applied directly in the corresponding prepared flat resected surfaces of the distal femoral bone. Accordingly, flat strips of bone cement can be applied and cover flat resected bone without further manipulation of the bone cement, i.e., without having to flatten and spread the delivered bone cement. Each flat strip of bone cement can be terminated or cleanly cut to a desired length by pinching it with the edge of the distal opening 114.

Figure 11:
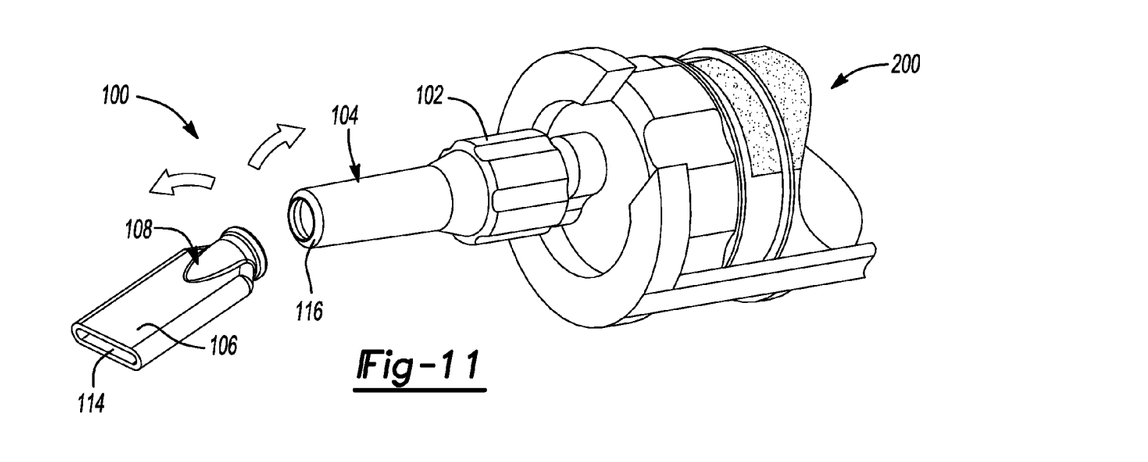
FIG. 11 is a perspective environmental view of a bone cement nozzle according to the present teachings showing breaking the bone cement nozzle along a frangible groove.
Figure 12:
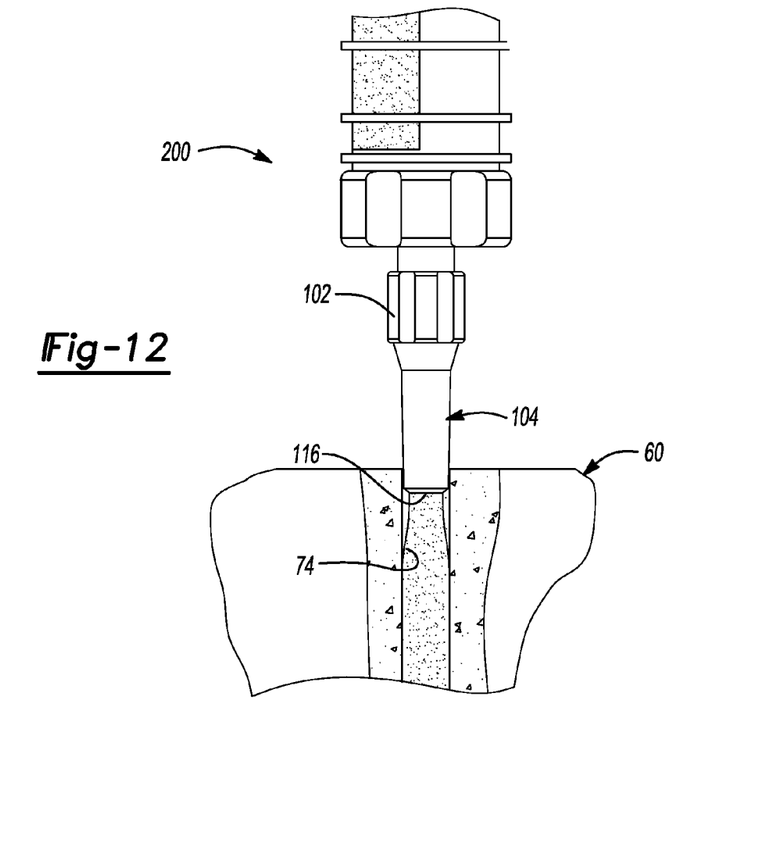
FIG. 12 is a perspective environmental view of the bone cement nozzle used for a filling a stem hole in a tibia after the distal portion is broken off.

FIG. 11 illustrates breaking off the distal portion 106 of the bone cement nozzle 100 by applying tension by bending on the frangible location 110 at the groove 112. Breaking off the distal portion 106 exposes a clean circular distal opening 116 of the intermediate portion 104. The newly exposed distal opening 116 of the intermediate portion 104 can be used to deliver bone cement in anchorage holes or stem holes in bone or in an intramedullary canal. FIG. 12 shows an example of using the new distal opening 116 to apply bone cement into a hole 74 prepared on the proximal surface of the tibial bone 60 for receiving a central peg of a tibial implant component (not shown). Bone cement can be similarly delivered into an intramedullary bone canal using the new distal opening 116.

Summarizing, the bone cement nozzle 100 of the present teachings can be used to deliver flat strips 82 of bone cement 80 of predetermined width and thickness for covering easily and efficiently a bone surface or a bone engagement surface of an implant component associated with an arthroplasty procedure without further manipulation of the delivered bone cement. The distal portion 106 of the bone cement nozzle 100 can be easily broken off at a frangible location 110 that is configured to expose a clean circular opening 116 at the distal end of the elongated intermediate portion 104 for delivering bone cement into holes for pegs or stems of implant components associated with the arthroplasty. Additionally, the elongated intermediate portion 104, after it is broken off the distal portion 106, can be coupled for use with other cementation nozzles, cement preparation nozzles or cement pressurizers, such as those provided in commercially available bone cement kits, such as, for example, the Optivac© system and/or the Optipac© system available from Biomet Manufacturing Corp., Warsaw, Ind., U.S.A.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. In this respect, the bone cement nozzle 100 of the present teachings can be provided in a kit including any combination of with bone cement, bone cement cartridge, bone cement mixer, bone cement gun, various bone cementation nozzles for the tibial and or femoral bone, separate bone cement pressurizers, and plugs or seals of various sizes for intramedullary canal applications.

The bone cement nozzle 100 can be made of biocompatible material, such as polyethylene, for example.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of applying bone cement for an orthopedic procedure of a patient comprising:
    coupling a proximal end of a nozzle component to a bone cement applicator;
    applying bone cement on a planar surface of an implant through a distal portion of the nozzle component, the distal portion having an elongated cross-section and defining an elongated distal opening;
    separating the distal portion of the nozzle component from an intermediate portion of the nozzle component at a frangible connecting portion, the intermediate portion having a circular cross-section; and
    exposing a distal end of the intermediate portion having the circular cross-section and defining a circular distal end including an opening for delivering cement to a different location.

2. The method of claim 1, wherein separating the distal portion comprises breaking off the distal portion at a circular groove formed between the intermediate portion and the connecting portion.

3. The method of claim 1, further comprising applying bone cement through the elongated distal opening to a resected bone of a patient.

4. The method of claim 1, wherein delivering bone cement to a different location includes discharging bone cement through the circular distal end of the intermediate portion into a hole in a bone of the patient.

5. The method of claim 4, wherein discharging bone cement to the hole in the bone comprises delivering bone cement into the hole for an anchoring member of the implant.

6. The method of claim 1, wherein applying bone cement on a planar surface of an implant comprises applying bone cement to a knee femoral implant component or a tibial knee implant component.

7. The method of claim 1, further comprising delivering flat strips of bone cement through the elongated distal opening without further manipulation of the bone cement after delivery.

8. The method of claim 1, wherein the intermediate portion is tapered.

9. The method of claim 1, wherein the elongated cross-section has a width greater than the diameter of the circular cross-section.

10. A method of applying bone cement for an orthopedic procedure of a patient comprising:
    coupling a proximal end of a nozzle component to a bone cement applicator, the nozzle component including an elongated intermediate portion having a circular cross-section and a longitudinal axis, the elongated intermediate portion in the form of a truncated cone having a variable diameter along the longitudinal axis thereof, a connecting portion extending from the intermediate portion at a frangible location, and a distal portion having an elongated cross-section;
    applying flat strips of bone cement on a surface of a first bone through an elongated distal opening of the distal portion of the nozzle component, each flat strip having a predetermined width and thickness;
    breaking the distal portion off the intermediate portion of the nozzle component at the frangible location to form a distal end with a circular cross-section; and
    delivering bone cement to a hole of a second bone from the circular cross-section.

11. The method of claim 10, further comprising applying flat strips of bone cement on a bone-engagement surface of an implant through the elongated distal opening of the distal portion of the nozzle component before breaking off the distal portion.

12. The method of claim 11, wherein the implant is a knee implant.

13. The method of claim 10, wherein the first bone is the same as the second bone.

14. The method of claim 10, wherein the one of the first and second bones is a femoral knee bone and the other is a tibial knee bone.

15. The method of claim 10, wherein applying flat strips of bone cement on a surface comprises delivering flat strips of bone cement without further manipulation of the bone cement after delivery.

16. The method of claim 10, further comprising inserting the distal end with the circular cross-section into an intramedullary canal for delivering bone cement into the intramedullary canal.

17. The method of claim 10, wherein breaking the distal portion off comprises breaking off the distal portion at a circular groove formed between the intermediate portion and the connecting portion.

18. The method of claim 10, wherein the frangible location includes a circular groove formed between the intermediate portion and the connecting portion.

* * * * *